(12) United States Patent
Unsworth et al.

(10) Patent No.: US 6,312,461 B1
(45) Date of Patent: Nov. 6, 2001

(54) SHAPE MEMORY TUBULAR STENT

(76) Inventors: John D. Unsworth, 365 Lodor St., Ancaster (CA), L9G 2Z5; Thomas C. Waram, 1063 King St., West, Suite 204, Hamilton (CA), L8S 1L8

(*) Notice: Subject to any disclaimer, the term of this patent is extended or adjusted under 35 U.S.C. 154(b) by 0 days.

(21) Appl. No.: 09/137,953

(22) Filed: Aug. 21, 1998

(51) Int. Cl.⁷ .................................................. A61F 2/00
(52) U.S. Cl. ............................... 623/1.19; 623/1.11
(58) Field of Search ........................... 623/1, 12, 1.18, 623/1.19, 1.11; 606/195, 192, 194

(56) References Cited

U.S. PATENT DOCUMENTS

| 5,102,417 | * | 4/1992 | Palmaz . | |
|---|---|---|---|---|
| 5,545,210 | * | 8/1996 | Hess et al. | 623/1 |
| 5,562,641 | * | 10/1996 | Flomenblit et al. | 604/281 |
| 5,653,747 | * | 8/1997 | Derume . | |
| 5,766,237 | * | 6/1998 | Cragg . | |
| 5,830,179 | * | 11/1998 | Mikus et al. | 604/49 |
| 5,849,035 | * | 12/1998 | Pathak et al. . | |
| 5,876,434 | * | 3/1999 | Flomenblit et al. | 623/1 |

FOREIGN PATENT DOCUMENTS

WO 9822042  5/1998  (WO) .

* cited by examiner

Primary Examiner—Michael J. Milano

(57) ABSTRACT

A stent radially expandable from a radially contracted introduction state into a radially expanded position state, in which the final shape of the stent can be controlled by varying the amount and places photo-thermal energy is projected onto the interior surfaces of the tubes from which the stent is fabricated.

15 Claims, 4 Drawing Sheets

SHAPE MEMORY TUBULAR STENT

FIELD OF THE INVENTION

This in invention relates to a stent for dilating and keeping open vessels, with a radially contracted state for introduction into the vessel and with a radially expanded stent after introduction into the vessel.

BACKGROUND AND SUMMARY OF INVENTION

Such stents or implantable catheters to be introduced into a body cavity, a vessel or the like can be made from plastic or an inert metal, such as steel or nickel-titanium alloys. Such stents are also referred to as endovascular or endoluminal stents or endoprostheses. For example, when dilating the ureter, the stents are used in the prostate region. In the case of benign prostate hyperplasia (BPH) or also in sclerotic blood vessels for dilating and keeping open the same. The stents have material areas and gaps between them. Thus, it is possible for the wall tissue of the organ kept open to grow round the stent. Stents can have a spiral construction, can be in the form of a helically wound coil or be in the form of a mesh fashioned from interconnected ribs. They can be made from woven or knitted wire or plastic material. Such stents can have memory properties, such as e.g. exist with certain nickel-titanium (nitinol).

A method of shaping a hollow tube after it has been placed in the body lumen is described Unsworth and Waram in a copending patent application, Ser. No. 08/749661 filed on Nov. 15, 1996, which patent application is incorporated herein by specific reference. That patent describes a method of imparting virtually any shape on a shape memory alloy (SMA) tube, or a tube made of material having similar materials that exhibit shape recovery when heated to an appropriate temperature. That patent application describes a device comprised of a side-firing laser or electrical probe that selectively heats parts of the inside of a tube of SMA material. By shape setting the tube to the desired shape at high temperature, then deforming the tube after it has cooled below the temperature at which it completely or nearly completely changes into its martensitic phase, one can create many shapes by heating part or parts of the tube to the temperature at which the selected parts of the material is transformed into its austenitic phase, thus recovering parts of the shape set into the tube at high temperature. That patent application described how a tube might be transformed into a coil stent it did not describe how a multiplicity of tubes might be formed into a mesh stent.

Any number of tubes can be arranged with their longitudinal axes parallel and their sides connected to each other at various places to form the walls of a larger tube. This larger tube can the be radially expanded by causing the smaller tubes to bend between the points of connection forming a webbed tubular structure. If the tubes are made of shape memory alloy (SMA) the larger webbed tube can be heat treated to its shape set temperature and when subsequently cooled below the martensitic finish temperature it can be radially formed into a more compact structure. After the shape setting and deformation steps, the expanded tubular structure can be recovered by heating it above the austenitic finish temperature.

In its compact martensitic form, the webbed tube can be inserted into the lumen of a tubular body, then heated to support the walls forming the lumen.

The shape of the tubes forming the webbed tubular structure can each be recovered utilizing the method described Unsworth and Waram in a copending patent application, Ser. No. 08/749661 filed on Nov. 15, 1996, which patent application is incorporated herein by specific reference. This method involves heating the SMA tubes with photo-thermal energy produced by a laser and delivered down an optical fiber. The photo-thermal energy is projected to the inside of the tubes at the distal end of the optical fiber by means of side-firing optics attached to the distal end of the fiber or incorporated into the distal end of the fiber. The area of projection can be varied depending upon the requirements of the particular application, by means of adjusting the optical side-firing means, means which are all well known to practitioners of the art.

As the optical fibers are withdrawn from the tubes, the optical fibers can apply photo-thermal energy to the inside of the tubes or while stationary in the tubes. Each fiber can be controlled individually, and depending upon whether or not the tube is heated and the shape is thereby recovered at a particular point, the shape of the entire webbed structure can be varied to best effect the purpose.

Short webbed tubular structures can be used in combination, being arranged end to end and being slidably attached only by the optical fibers that pass through their lumens. The optical fibers keep the sections of tubular structures aligned, but allow the train of sections to flex around curves in the body lumen. The flexibility of the train can be controlled by varying the ease with which the fibers slide within the lumens of the tube. By this means the train of webbed tubular structures can be made stiff or very flexible, depending upon the requirements of the case.

It can be readily be seen that the stent fabricated from tubes as described, whether in one piece or a train of sections, offers the advantage of being able to vary the final shape of the stent by varying the parts of the webbed structure that are recovered. In the case of a train of sections, each can be deployed sequentially and separations between them can be controlled, either in advance, by their placement on the distal end of the catheter, or on the fly, by withdrawing the delivery catheter a desired distance, between deployments of the sections.

Further advantages and features of the invention can be gathered from the claims and description of a preferred embodiment of the invention with reference to the drawings.

DETAILED DESCRIPTION OF THE INVENTION

Figure 1:
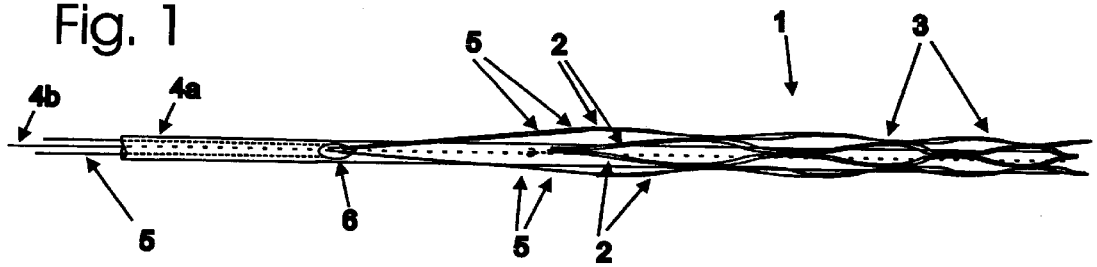
FIG. 1 is a perspective view of the preferred embodiment of the stent in its radially contracted low temperature or introduction state. For diagrammatic clarity, the tubes in the background are drawn with a thinner pen nib that the tubes in the foreground and only four of the eight optical fibers are shown.

In its radially contracted state for introduction into the body lumen to be dilated or supported, the stent 1 is a webbed tubular structure or an outer contour as shown in FIG. 1. The eight tubes 2 are connected at nodal points 3 by welds or other connecting means. The stent is delivered into the body lumen at approximately the distal end of a delivery catheter 4 to which it is detachably attached. Although the preferred embodiment of the invention shown in FIG. 1 is comprised of eight tubes, any number of tubes could comprise the webbed tubular structure.

Figure 2:
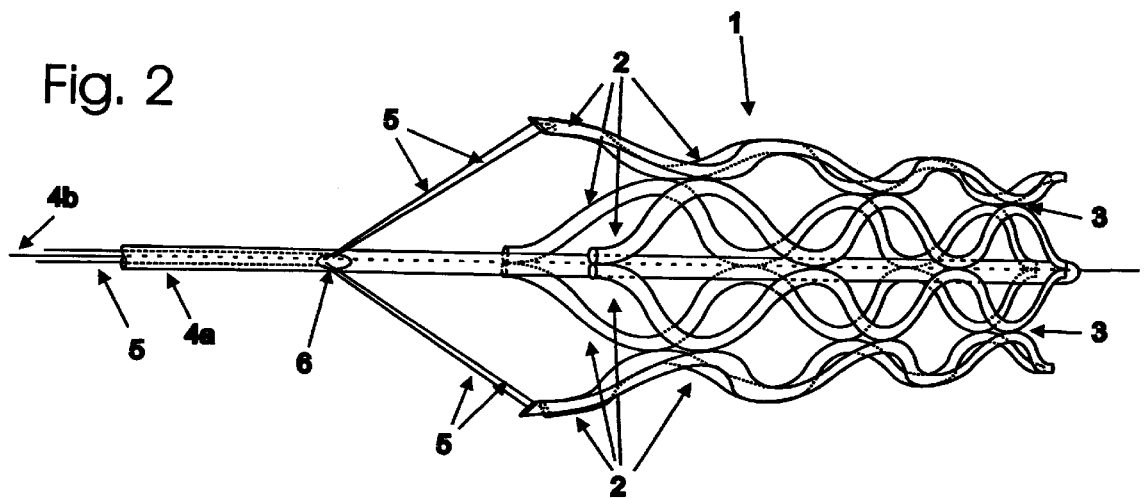
FIG. 2 is a perspective view of the same stent according to the invention in its radially expanded high temperature or use state and shows the delivery catheter and the optical fibers passing from orifices in the delivery catheter to the lumens of the tubes forming the stent.
Figure 3:
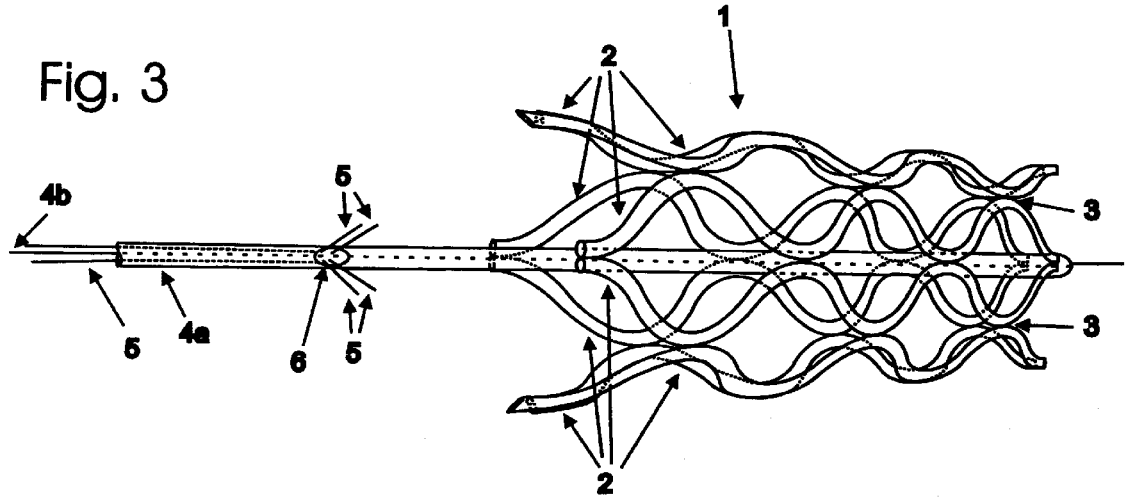
FIG. 3 is a perspective view of the same stent as shown in FIG. 1 and FIG. 2 but with the optical fibers withdrawn from the stent and just about to be drawn by the operator into the catheter.

In the radially expanded shape as shown on FIG. 2 the tubes 2 have had their shapes recovered by the application of photo-thermal energy delivered by optical fibers 5 from a photo-thermal source coupled to the proximal end of the said optical fiber. The optical fibers that deliver the photo-thermal energy that initiate the shape recovery pass through the delivery catheter and exit it at orifices 6 of the said delivery catheter and thence into the lumens of the tubes 2. The application of photo-thermal energy by means of side-firing optical fibers can be controlled by a method taught by Unsworth and Waram in a copending patent application, Ser. No. 08/749661 filed on Nov. 15, 1996. The application of photo-thermal energy to the inside surfaces of the lumens of the said tubes 2 can be accomplished by various procedures. For example, the side-firing optical fiber can project a narrow beam of photo-thermal energy onto the inside surface of the lumen of the said tubes 2, in which case the optical fiber typically would be withdrawn gradually from the lumen of the said tubes or individual tubes by the operator and the shape recover would proceed gradually from one end of the distal end of the tube being recovered to the proximal end of the said tube. Another example would be a side-firing optical fiber that would project a broad beam onto the entire length of the said tube 2. In this second example the entire length of the tube would recover its shape at the same time. A further example would be a side-firing optical fiber that has multiple side-firing or leaking elements along the fiber at intervals or an end firing optical fiber. Obviously the breadth of the beam projected, the number of beams and the way in which the operator chooses to apply the photo-thermal energy to each tube together or individually make possible many combinations that will be available depending upon the requirements of the procedure at hand.

Figure 4:
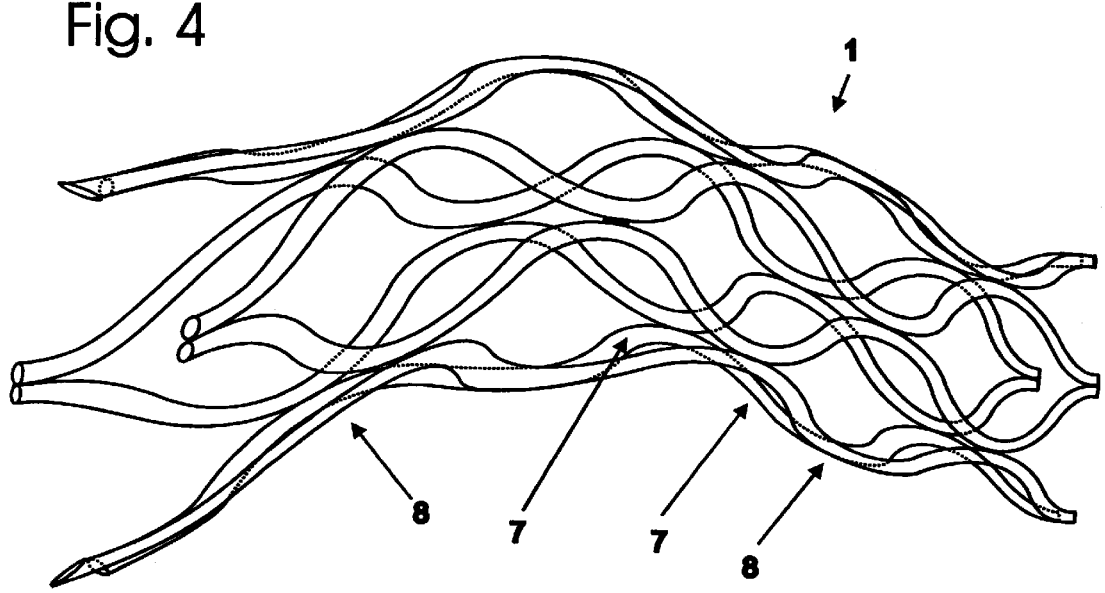
FIG. 4 shows the same stent as shown in FIG. 3 except that the bottom two tubes have not been fully recovered causing the tubular structure to bend.
Figure 9:
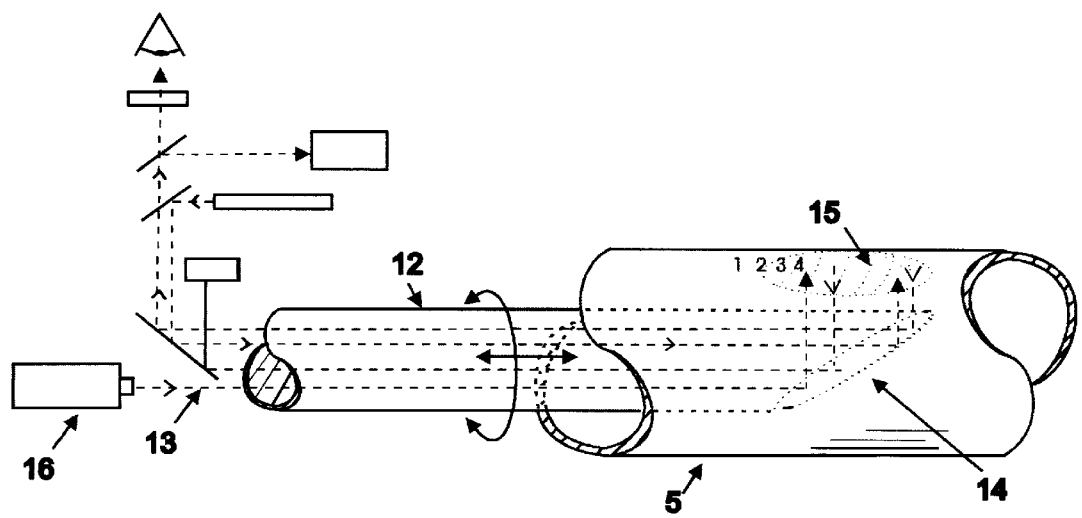
FIG. 9 is a perspective view of a device used in combination with a method taught by Unsworth and Waram in a copending patent application, Ser. No. 08/49661 filed on Nov. 15, 1996 for applying thermal energy to the inside of SMA tubes to recover parts of the shape that was fixed into them at high temperature.

FIG. 4 ;shows only one simple example of the control over the final shape of the stent that is possible by varying the application of photo-thermal energy onto the inside surface of individual tubes 2 that comprise the stent. The effect of reducing the amount of photo-thermal energy on particular tubes that would otherwise be necessary to fully recover the shape of the tubes is illustrated in FIG. 4 where the tubes 7 and 8 have not fully recovered and thus are straighter than those other fully recovered tubes forming the tubular web stent. The straighter tubes cause the stent to bend as illustrated on FIG. 4. This permits tailoring the shape of the stent to the particular shape of the body lumens into which it is inserted and expands. It may also be advantageous to vary the shape of the stent prior to its deployment to position it within the body lumen. It should be apparent that the stent can be shaped in myriad different ways using this technique depending upon the original shapes fixed into the SMA and the parts of the tubes that are heated utilizing the methods Unsworth and Waram in a copending patent application, Ser. No. 08/749661 filed on Nov. 15, 1996, which patent application is incorporated herein by specific reference and the device described in that said patent application and illustrated in FIG. 9 is included herein for reference purposes.

Figure 5:
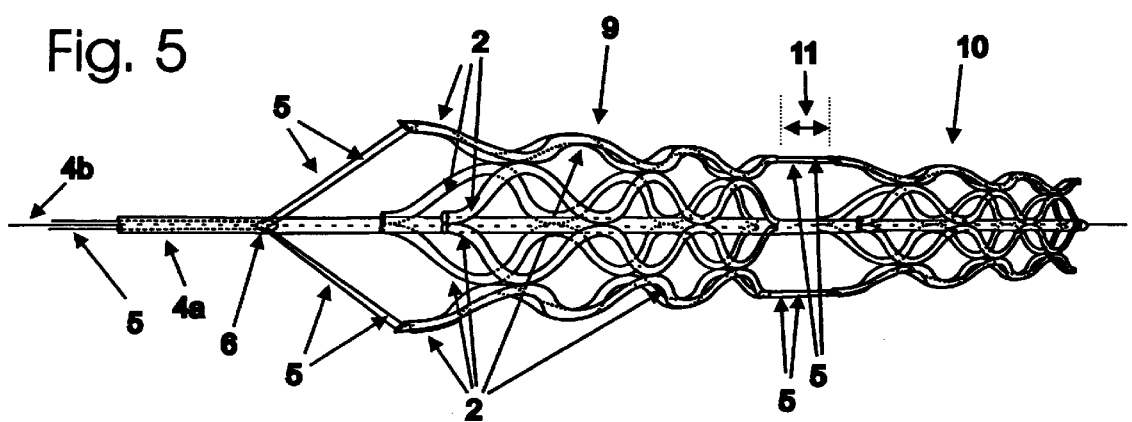
FIG. 5 shows a train of stent sections, slidably attached and aligned by the optical fibers passing through the lumens of the tubes that form the stent.
Figure 6:
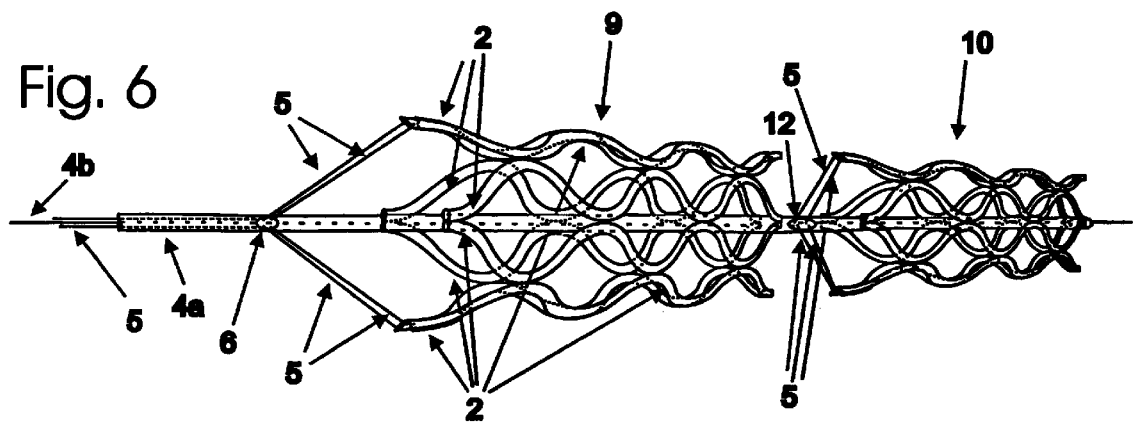
FIG. 6 is a perspective view of the same stent sections as shown in FIG. 5, except that the optical fibers for the distal section, like the proximate section, pass directly from the orifices in the delivery catheter to the lumens of the tubes forming the said stent section.
Figure 7:
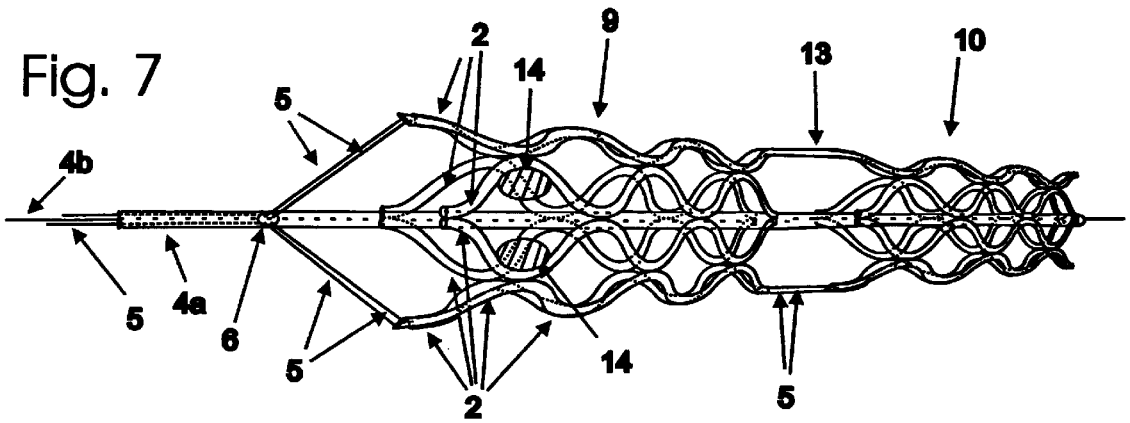
FIG. 7 is a perspective view of the same stent sections as shown in FIG. 6 except that one of the tubes is common to both stent sections.

As illustrated in FIG. 5 stent sections 9 and 10 can be assembled end to end on the delivery catheter 4. Again, for diagrammatic clarity, only four of the optical fibers 5 are shown, rather than one for each of the tubes in the stent assembly. Although FIG. 5 shows only two sections, additional sections could be added and each section could vary in dimension, including the number of tube meanders. The optical fibers that deliver photo-thermal energy to the distal section 10 can either first pass through the proximal section 9 as shown in FIG. 5 or can go directly to a second orifice 12 in the delivery catheter 4. In the former case the fiber that passes through the distal section 10 can be the same as that which passes through proximal section 9 or it can be a separate optical fiber. The use of a train of smaller stent sections has several advantages. The principle advantage is that it is more flexible than a single larger section. This makes it easier to deliver to the site of deployment if the lumen into which it was inserted is convoluted. Another advantage is that spaces can be left between sections that would accommodate vessel side branches. As shown on FIG. 5 the sections are slidably attached by optical fibers 5. The relative sizes of the optical fibers 4 and the lumen of the tubes will determine the resistance to the removal of the optical fiber as it is withdrawn from the tubes. This will also affect the flexibility of the joint formed by the optical fibers between the sections 9 and 10. Thus the flexibility of the joint can be controlled by varying the relative size of the optical fiber and the lumen of the tubes, varying the relative flexibility of the optical fibers to that of the tubes and by varying the length of the separation 11 between the sections 9 and 10. An additional means of increasing the rigidity of the joint between the sections is to continue one or more, of the tubes from one section to the other as shown in FIG. 7 which shows one tube 13 that is continuous between sections 9 and 10. In addition to controlling the flexibility of the said joint between the said sections, these means also assist in aligning the stents with respect to one another.

FIG. 7 also shows a set of scales or plates 14 that are connected to two tubes 2 to increase the surface area of the stent that comes into contact with the inner surface of the vessel into which the stent is placed. While FIG. 7 depicts only one set of scales, any number of scales could be added to the stent for this purpose. To accommodate the scales when the stent is in its contracted state, as illustrated in FIG. 1, the scale ends could interleave or overlap. The scales could also extend over more than one meander. Thus, It would be possible to cover the entire surface area of the webbed tubular structure with one or more scales.

Figure 8:
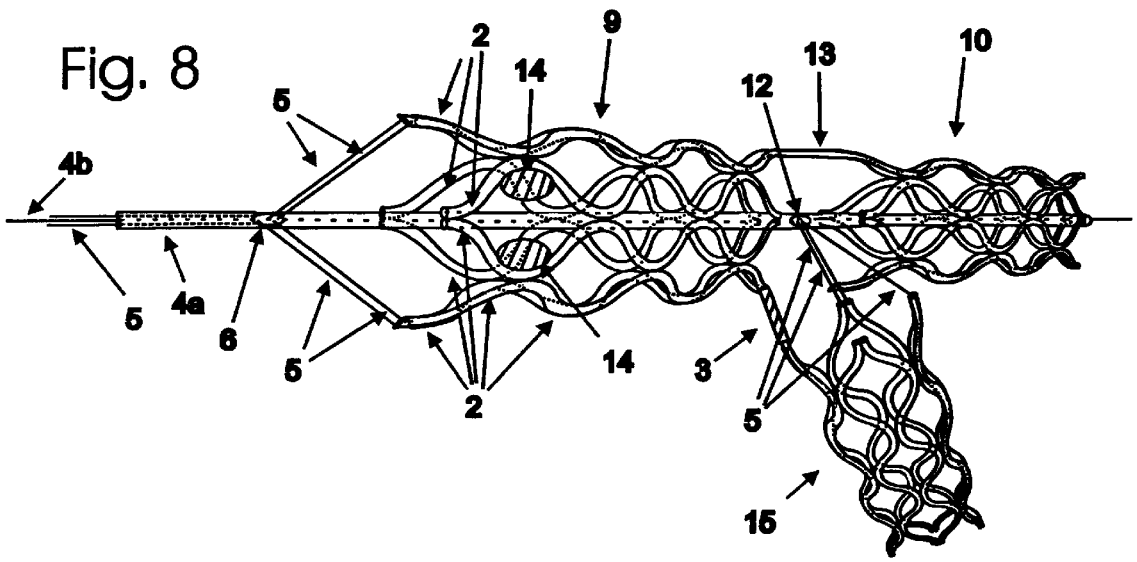
FIG. 8 is a perspective view of the same stent sections as shown in FIG. 7 except that an additional stent section has been connected to one of them for the purpose of supporting or enlarging bifurcated vessels.

The stent sections illustrated in FIG. 8 address the difficult problem of supporting or enlarging bifurcated or branched vessels. The additional stent section 15 is connected by a weld or connecting element 3 to stent section 9, but could a continuation of a tube in stent section 9. For diagrammatic clarity only four optical fibers 5 are shown running from the orifice 6 in the delivery catheter 4a into the lumens of four of the tubes comprising stent section 15, although in the preferred embodiment each tube comprising stent section 15 would have an optical fiber to deliver photo-thermal energy to the tube as required. The stent sections 9, 10 and 15 typically would be inserted into the vessel in their compressed state and then stent sections 10 and 15 would be partly splayed by applying photo-thermal energy at approximately the location of the connection 3 between stent section 9 and 15. Once partly splayed the stent assembly could be advanced distally into the vessel and additional photo-thermal energy could be applied to completely splay the said sections 9 and 15 to permit the final distal advancement of the assembly into the bifurcated vessel. Once the stent assembly is completely splayed the remainder of the expanded shape of the entire stent sections could be fully recovered as shown in FIG. 8. Although the above procedure mentions two steps in recovering the splayed shape, any number of incremental steps might be taken to effect the desired result, depending upon the circumstances. As can be readily appreciated any number of stent assemblies can be connected by means similar to those described to form myriad shapes for various purposes.

In the preferred embodiment of the invention the stent 1 is made from a nickel-titanium alloy, such as Nitinol, although any other material that exhibits shape recovery on the application of photo-thermal energy would be included within the preferred embodiments of the invention. The expanded shape shown in FIG. 2 is heat treated to give the stent memory properties, so that when cooled to its martensitic finish temperature it can be deformed into its radially contracted form as shown in FIG. 1, and then when it is heated to its austenitic finish temperature it will recover to its expanded shape shown in FIG. 2.

While the present invention refers to shape memory alloy tubes, sometimes referred to as just tubes, it is to be understood that the invention includes tubes made of other materials that exhibit shape recovery when heated to an appropriate temperature. The references to shape memory alloy should then be considered to be by way of example only of a larger class of materials that exhibit similar properties.

It should also be understood that while the examples of tubes referred to in this disclosure and in the drawings are cylindrical, it is to be understood that tubes having a cylindrical cross-section are only examples of a larger class of tubes having many different cross-sections for example, triangular, square or star-shaped a combination thereof.

It should also be understood that while reference is made to photo-thermal energy being delivered to the tubes, other forms of energy that could be directed down energy guides and that would have the effect of recovering the memorized shape could be substituted.

It should also be understood that a web shape fabricated from tubes is the preferred embodiment of the invention, web shapes can be created by weaving the tubes in different configurations, and other shapes can be formed from connected tubes that act in like manner and are included within the invention.

While the present invention has been described in conjunction with preferred embodiments, it is to be understood that modifications and variations may be resorted to without departing from the spirit and scope of the invention as those skilled in the art will readily understand. Such modifications and variations are considered to be within the purview and scope of the inventions and appended claims.

What is claimed is:

1. A stent deployment system, comprising:

at least one radially expandable stent means having a proximal end, a distal end and a lumen, each said stent means comprising a hollow, generally cylindrical member having a side surface comprising a mesh having a plurality of openings, said mesh being formed by at least one elongate member comprised of a shape memory alloy having a martensite start temperature less than body temperature and an austenite finish temperature above body temperature, said at least one elongate member having a memorized shape which is recovered when said elongate member is heated to said temperature above body temperature, said at least one elongate member having a lumen;

delivery means adapted to convey the at least one stent means to a lumen of a vessel; and heating means adapted to heat at least a portion of said at least one elongate member to said temperature above body temperature to at least partially recover said memorized shape, said heating means comprising at lest one optical fiber, each said optical fiber extending into the lumen of a respective one of said elongate members and being adapted to transmit photo-thermal energy onto at least part of an inner surface of the elongate member;

wherein said memorized shape is selected so that shape recovery of said at least one elongate member results in radial expansion of said at least one stent means inside the lumen of the vessel.

2. The stent deployment system of claim 1, wherein said at least one elongate member comprises a plurality of tubular members each having a proximal end and a distal end, the tubular members extending longitudinally along the stent means.

3. The stent deployment system of claim 2, wherein each of the tubular members is joined at a plurality of points along its length to two other of the tubular members.

4. The stent deployment system of claim 3, wherein the points are regularly spaced.

5. The stent deployment system of claim 4, wherein each of the tubular members defines a regular wave-form having alternating crests and valleys, and wherein the crests of each of the tubular members is joined to the valleys of another of the tubular members.

6. The stent deployment system of claim 5, wherein each tubular member has a memorized shape in which a difference in height between the crests and the valleys of the wave-form is greater than the difference in height when the stent means is in a radially compressed state.

7. The stent deployment system of claim 1, wherein the delivery means comprises a delivery catheter having a proximal end and a distal end, and the at least one stent means is releasably attached to the distal end of the delivery catheter, with the distal end of the catheter extending into the lumen of the at least one stent means.

8. The stent deployment system of claim 7, wherein each said optical fiber enters the delivery catheter at the proximal end thereof and exits the delivery catheter through an orifice provided in the delivery catheter at a distal end thereof, the orifice being longitudinally spaced from the proximal end of the stent means, said catheter having at least one of said orifices.

9. The stent deployment system of claim 8, wherein the stent means is releasably connected to the delivery catheter by said at least one optical fiber, and wherein said at least one optical fiber is retractable into said orifice of the delivery catheter to thereby separate the stent means from the catheter.

10. The stent deployment system of claim 8, wherein said at least one stent means comprises at least two stent means, wherein a first of the stent means is provided longitudinally spaced from a second of the stent means, the first stent means being closer to the proximal end of the catheter than the second stent means.

11. The stent deployment system of claim 10, wherein each of the two stent means is directly connected to the delivery catheter by at least one of said optical fibers, and wherein the optical fibers are retractable into the delivery catheter to separate the stent means from the catheter.

12. The stent deployment system of claim 10, wherein the first stent means is releasably connected to the delivery catheter by said at least one optical fiber, and wherein said at least one optical fiber extends through the distal end of the first stent means and into the proximal end of the second stent means, thereby releasably connecting the first and second stent means to one another, the at least one optical fiber being retractable into the delivery catheter to separate the stent means from the catheter.

13. The stent deployment system of claim 10, wherein the first and second stent means are connected by at least one tubular member extending from the proximal end of the first stent means to the distal end of the second stent means.

14. The stent deployment system of claim 3, wherein an external surface of the side surface of the stent means is provided with plate means at least partially covering the openings.

15. The stent deployment system of claim 13 adapted to be received at a branch of said vessel, further comprising a third stent means having a distal end, a proximal end and a lumen, the proximal end of the third stent means positioned at a gap between said first and second stent means, said distal end of said catheter extending through said gap outwardly of the lumen of the third stent means, such that a longitudinal axis of said third stent means is angled relative to a longitudinal axis of the first and second stent means, wherein said third stent means comprises a generally cylindrical member having a side surface comprising a mesh having a plurality of openings, said mesh being formed by at least one elongate member comprised of a material having shape memory characteristics, said at least one elongate member having a memorized shape which is recovered when said elongate member is heated to a temperature above body temperature, wherein said third stent means is releasably connected to said distal end of said catheter by at least one of said optical fibers.

* * * * *